United States Patent
Iyengar et al.

(10) Patent No.: US 10,285,633 B2
(45) Date of Patent: May 14, 2019

(54) IMPLANTABLE ELECTROCHEMICAL BIOSENSOR SYSTEM AND METHOD

(71) Applicant: AgaMatrix, Inc., Salem, NH (US)

(72) Inventors: Sridhar Iyengar, Salem, NH (US); Ian Harding, Wells (GB)

(73) Assignee: AgaMatrix, Inc., Salem, NH (US)

( * ) Notice: Subject to any disclaimer, the term of this patent is extended or adjusted under 35 U.S.C. 154(b) by 0 days.

(21) Appl. No.: 15/910,251

(22) Filed: Mar. 2, 2018

(65) Prior Publication Data

US 2018/0249938 A1 Sep. 6, 2018

Related U.S. Application Data

(60) Continuation of application No. 15/069,071, filed on Mar. 14, 2016, now Pat. No. 9,907,501, which is a continuation of application No. 14/601,851, filed on Jan. 21, 2015, now Pat. No. 9,375,173, which is a division of application No. 12/882,761, filed on Sep. 15, 2010, now Pat. No. 9,907,499.

(60) Provisional application No. 61/242,509, filed on Sep. 15, 2009.

(51) Int. Cl.
| | |
|---|---|
| A61B 5/00 | (2006.01) |
| A61B 5/1486 | (2006.01) |
| C12Q 1/00 | (2006.01) |
| A61B 5/145 | (2006.01) |
| A61B 5/1495 | (2006.01) |

(52) U.S. Cl.
CPC ........ *A61B 5/14865* (2013.01); *A61B 5/1495* (2013.01); *A61B 5/14532* (2013.01); *A61B 5/7225* (2013.01); *C12Q 1/001* (2013.01); *C12Q 1/006* (2013.01)

(58) Field of Classification Search
CPC ..... A61B 5/14532; C12Q 1/001; C12Q 1/006
See application file for complete search history.

(56) References Cited

U.S. PATENT DOCUMENTS

| | | | |
|---|---|---|---|
| 4,431,004 | A | 2/1984 | Bessman et al. |
| 6,081,736 | A | 6/2000 | Colvin et al. |
| 6,119,028 | A | 9/2000 | Schulman et al. |
| 6,162,611 | A | 12/2000 | Heller et al. |
| 6,387,048 | B1 | 5/2002 | Schulman et al. |
| 6,466,810 | B1 | 10/2002 | Ward et al. |
| 6,514,718 | B2 | 2/2003 | Heller et al. |
| 7,108,778 | B2 | 9/2006 | Simpson et al. |
| 7,344,626 | B2 | 3/2008 | Harding et al. |
| 2005/0069892 | A1 | 3/2005 | Lyengar et al. |
| 2005/0109637 | A1 | 5/2005 | Lyengar et al. |
| 2005/0203361 | A1 | 9/2005 | Caduff et al. |
| 2006/0231418 | A1 | 10/2006 | Harding et al. |
| 2006/0231424 | A1 | 10/2006 | Harding et al. |
| 2006/0275859 | A1 | 12/2006 | Kjaer |
| 2007/0299617 | A1 | 12/2007 | Willis |
| 2008/0039702 | A1* | 2/2008 | Hayter ............... A61B 5/14532 600/345 |
| 2009/0068754 | A1 | 3/2009 | Wu et al. |

(Continued)

*Primary Examiner* — Christian Jang

(74) *Attorney, Agent, or Firm* — Larson & Anderson, LLC

(57) ABSTRACT

Correction for initial variation in thickness of a polymer layer and for changes in the coating thickness that occur after implantation of a biosensor and therefore provides substantial increase in the accuracy and lifetime of implantable sensors is done using a factor derived from the decay of potential.

20 Claims, 16 Drawing Sheets

(56) References Cited

U.S. PATENT DOCUMENTS

2009/0101498 A1 4/2009 Papadimitrakopoulos et al.
2009/0194432 A1 8/2009 Deng

* cited by examiner 20  21  22 distance

20

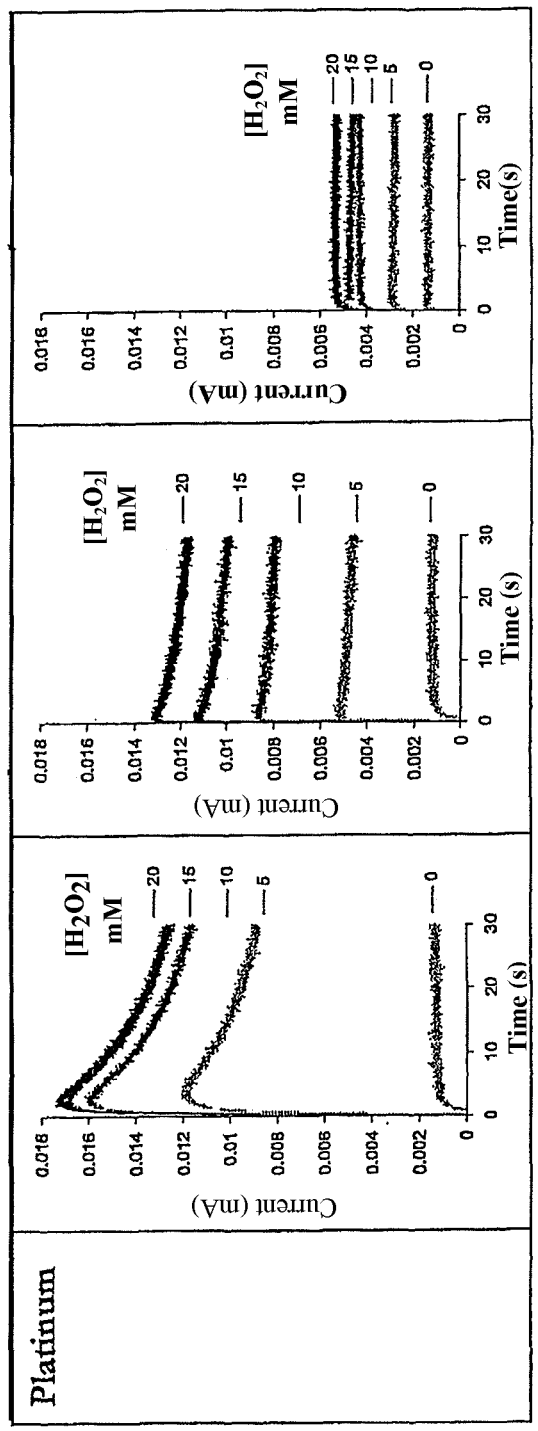

No Coat  Thin Coat  Thick Coat

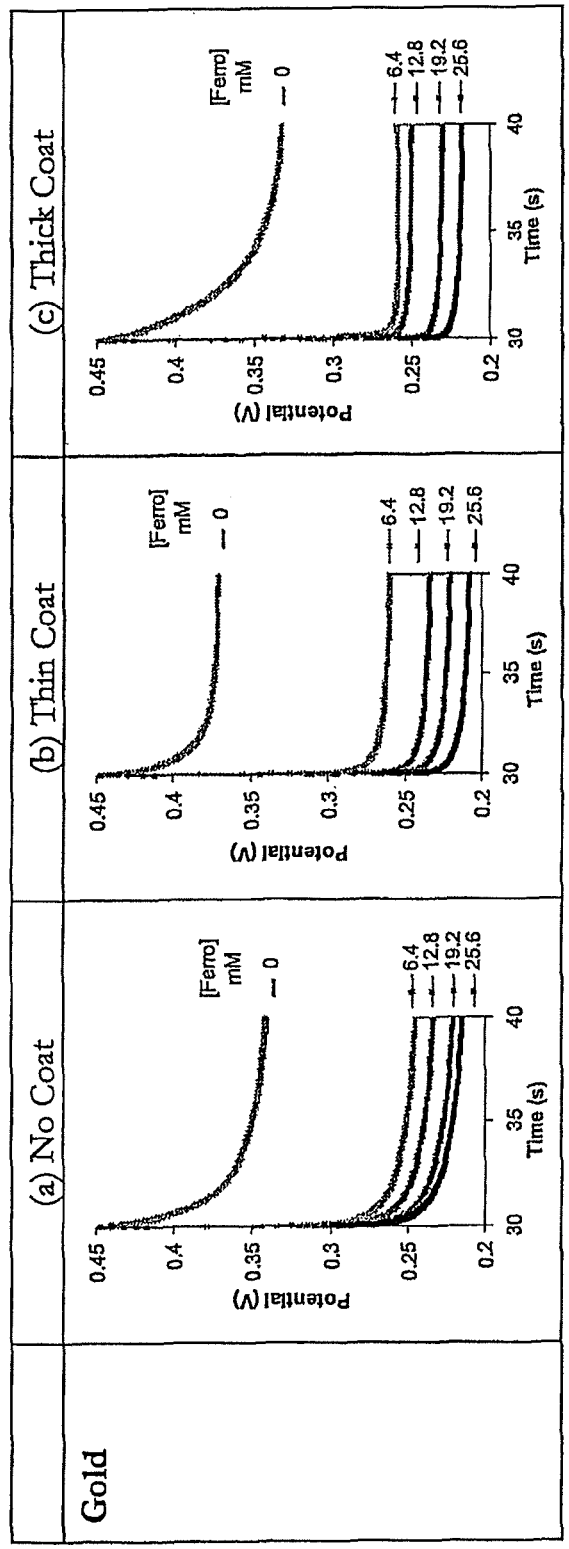

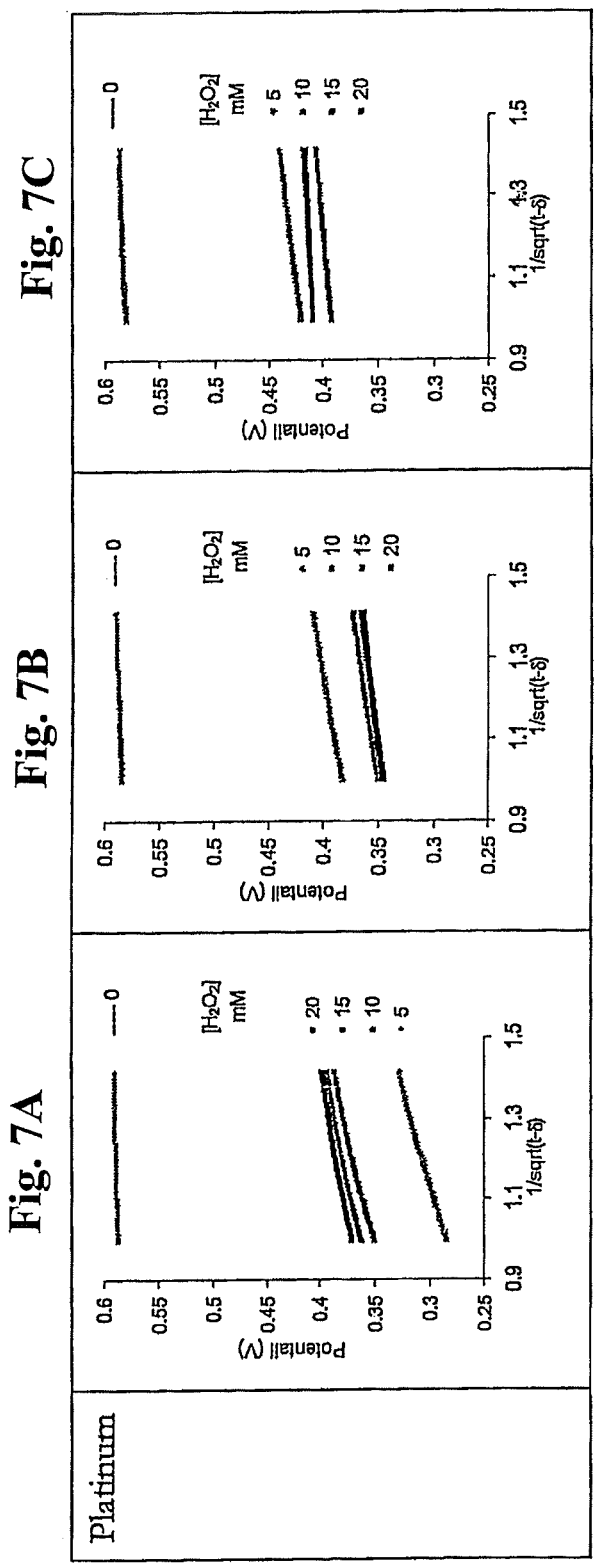

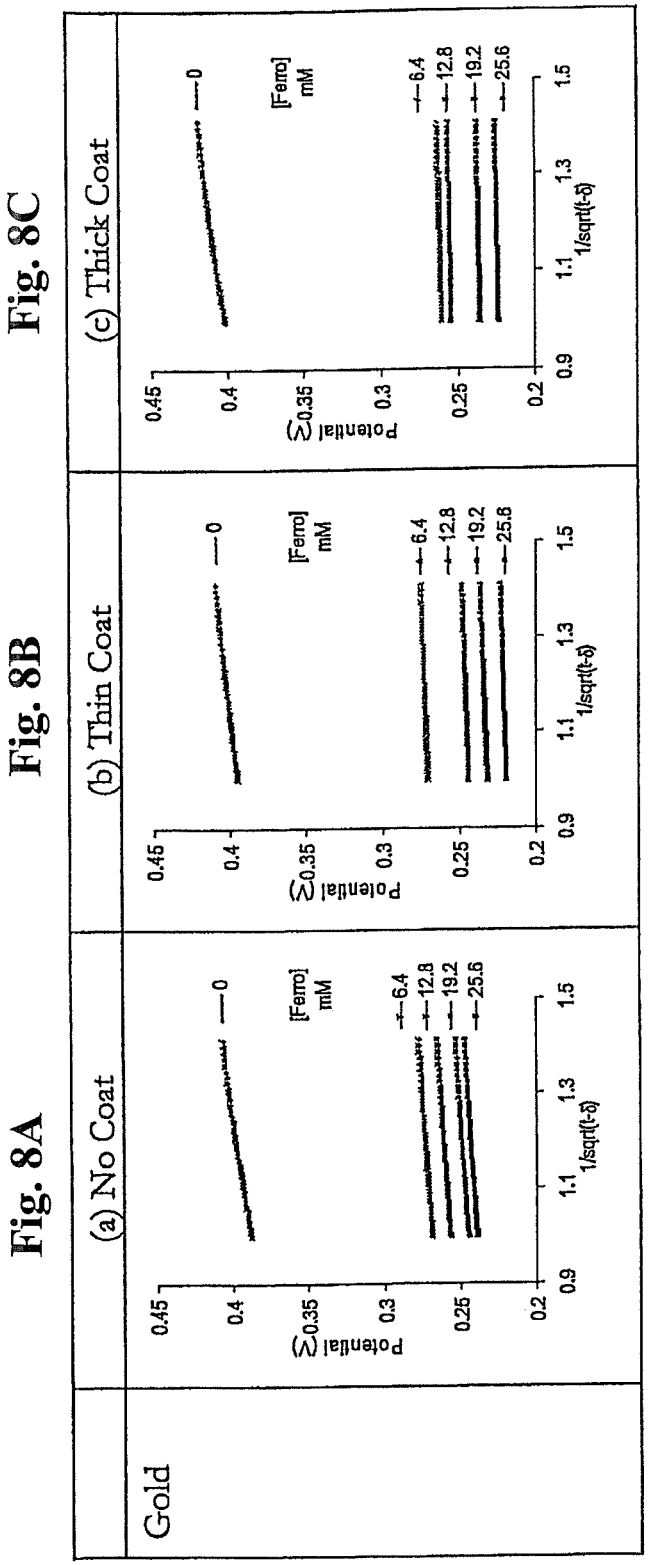

121  123        122 distance

IMPLANTABLE ELECTROCHEMICAL BIOSENSOR SYSTEM AND METHOD

RELATED APPLICATIONS

This application claims the benefit of U.S. Provisional Application No. 61/242,509 filed Sep. 15, 2009, which application is incorporated herein by reference in its entirety.

BACKGROUND OF THE INVENTION

This application relates to implantable biosensors, such as implantable biosensors used for monitoring of blood glucose levels.

Implantable electrochemical biosensors are known for detection of glucose and other analytes found in body fluid. (See, for example, U.S. Pat. Nos. 4,431,004, 6,081,736, 6,119,028, 6,162,611, 6,387,048, 6,466,810, and 7,108,778 and US Patent Publications 20060275859 all of which are incorporated herein by reference). In general, these sensors contain an electrode that is separated from blood or other body fluids by a polymer layer that is permeable to the analyte, but that maintains components such as enzymes that are necessary to the electrochemical detection of the analyte near the surface of the electrode. Analyte diffuses from the blood or body fluid into the polymer layer to be measured. By way of example, measurement of glucose can be performed using the reaction scheme shown in FIG. 1. Glucose is oxidized to gluconolactone in the presence of the enzyme glucose oxidase (GOx). The resulting reduced glucose oxidase is oxidized (and thus reactivated for further reaction with glucose) by oxygen with the resulting production of production peroxide. Peroxide is oxidized at the electrode, and the amount of glucose is reflected in the current generated by this oxidation. A polymer layer is disposed on the electrode to maintain the glucose oxidase in the vicinity of the surface of the electrode.

Error can arise in implantable sensors as a result of variations in the thickness of the polymer layer. Such variations in thickness may arise as a result of manufacturing variations. Variations in the thickness of additional layer that are part of the sensor may also give rise to differences in the observed signal. (See for example U.S. Pat. No. 6,514,718 which is incorporated herein by reference) Furthermore, once an implantable sensor is in use in the body, the surface of the polymer layer may become fouled with proteins or other cellular materials which increase the effective thickness of coating on the electrode and these changes will alter the performance of the electrode. Therefore, unless a correction is made, the error in measurements will increase over time, and the lifetime of the implanted sensor is limited.

The present invention provides for correction for initial variation in thickness of the polymer layer (i.e., manufacturing variation) and for changes in the coating thickness that occur after implantation and therefore provides substantial increase in the accuracy and lifetime of implantable sensors.

SUMMARY OF THE INVENTION

In accordance with the present invention, the presence or concentration of an analyte is determined by a method comprising the steps of:

(a) placing a solution to be tested for analyte in contact with a biosensor comprising an electrode and a polymer layer containing an enzyme, (b) applying a potential to the biosensor sufficient to oxidize or reduce a redox active species and generate a current, (c) observing the current to arrive at a measured current value, $I_{meas}$, (d) switching off the applied potential and observing subsequent decay of potential to obtain a plurality of V versus t data points, (e) determining the slope k of a plot of V versus 1/sqrt-t, and (f) applying a correction factor to the measured current $I_{meas}$ to arrive at a corrected current, $I_{corr}$, wherein the correction factor is 1/k if the redox active species is part of a reversible redox couple, and 1/sqrt-k if the redox active species is part of an irreversible redox couple, and (g) determining the presence or concentration of the analyte from the corrected current, $I_{corr}$.

The solution may be a biological fluid such as blood or interstitial fluid, which is placed in contact with a the biosensor by implanting of the sensor.

BRIEF DESCRIPTION OF THE FIGURES

FIGS. 3A-C shows show amperometric responses of a platinum electrode to different concentrations of $H_2O_2$ when the electrode is uncoated (FIG. 3A), thinly coated (FIG. 3B) and thickly coated (FIG. 3C).

FIGS. 6A-C shows potential decay over a period of 10 seconds after potential is turned off for the gold/ferro system, with uncoated, thin coated and thick coated electrodes.

FIGS. 7A-C show the data from FIGS. 5A-C plotted as V versus 1/sqrt-t.

FIGS. 8A-C show the data from FIGS. 6A-C plotted as V versus 1/sqrt-t.

DETAILED DESCRIPTION OF THE INVENTION

Definitions

Figure 1:
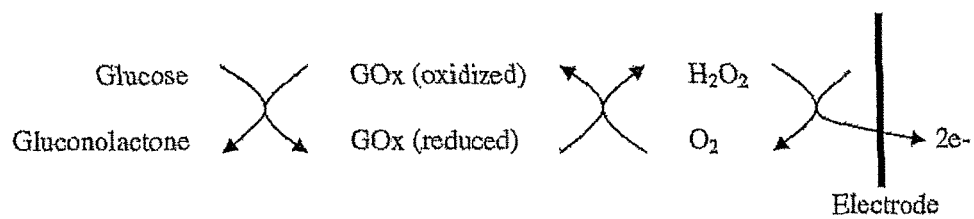
FIG. 1 shows the reactions involved in a peroxide-forming glucose detection reaction.

As used herein, the following terms should be understood to have meaning as follows: analyte refers to the material of interest in a sample that is detected by the implantable electrode. The analyte may be, for example, a chemical of biological significance such as glucose, lactate, cholesterol, fructose, alcohol, amino acids, creatine and creatinine.

detection of analyte in a sample refers to the qualitative, semi-quantitative or quantitative determination of whether an analyte is present in a sample at detectable levels. Qualitative analysis provides merely a yes/no answer as to whether there is detection. Semi-quantitative provides an indication of amount, but with high granularity, for example as presented through a series of lights where the number of lights illuminated indicates the range into which a value falls. Quantitative analysis provides a numerical value for the amount of analyte in the measured sample.

electrochemical biosensor refers to plurality of electrodes, generally to a pair of electrodes, that when connected to a means for applying potential or current between the electrodes provide an electrochemical signal which is indicative of an analyte in a sample. One of the electrodes in a biosensor include a redox enzyme that interacts with analyte. An implantable electrochemical biosensor is an electrochemical biosensor in which at least one of the electrodes has an analyte-permeable polymer layer for maintaining reagents such as the enzyme reagent in the vicinity of the electrode.

electrochemical biosensor system refers to the combination of an electrochemical biosensor and a control device which includes the means for applying potential or current between the electrodes of a connected electrochemical biosensor, means for observing the electrochemical signal indicative of analyte in a sample, and means for processing the observed signal to produce a determination of analyte.

polymer layer refers to an analyte-permeable polymeric coating that is disposed over the working electrode to maintain reagents such as the enzyme reagent in the vicinity of the working electrode of a biosensor when the electrode is implanted in contact with blood, other body fluids or tissue. "In the vicinity" means that the reagents remain localized in a volume where the results of their reactions can be monitored/observed by the electrodes during the intended period of taking measurements.

Method of the Invention

In accordance with the present invention, the determination of analyte can be made by either a potentiometric or an amperometric measurement. A correction factor for the thickness of the membrane/polymer layer is determined using a combination of both amperometric (applied potential, measured current) and potentiometric (applied potential turned off, potential measured) measurements. Signal processing approaches which make use of an initial application of potential to produce a measurable current, followed by turning the applied potential off and continuing with potential measurements are described in commonly assigned applications US 2005/0109637, US 2005/0069892, US 2006/0231424, and US 2006/0231418, all of which are incorporated herein by reference. These approaches are used in the context of in vitro testing however using disposable test strips and therefore are not concerned with correction for thickness of the membrane/polymer layer.

Figure 2A:
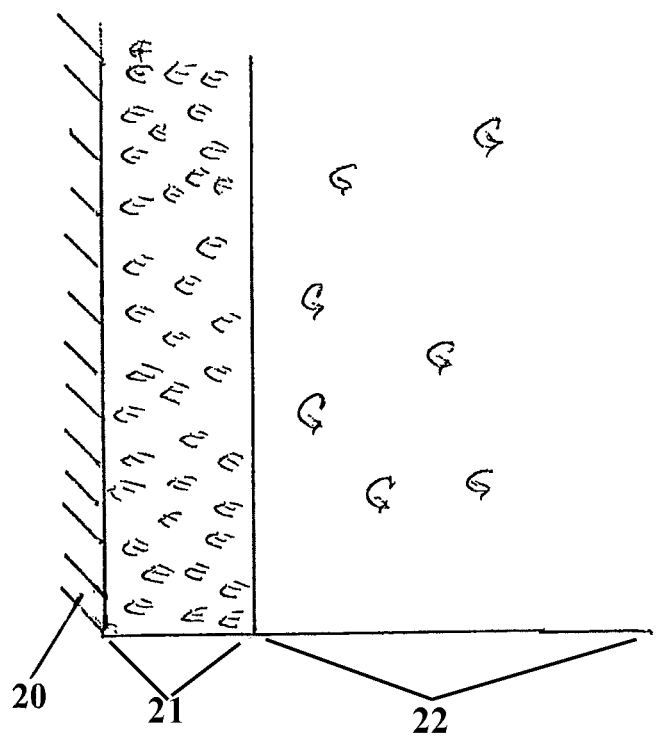
FIGS. 2A-C show the distribution of reagents in a polymer layer adjacent to an electrode surface.
Figure 2B:
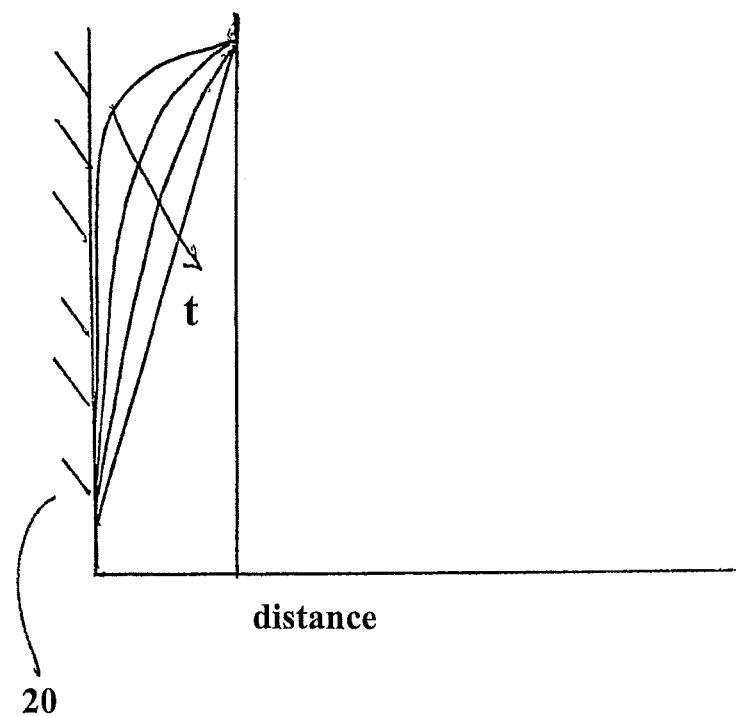
Figure 2C:
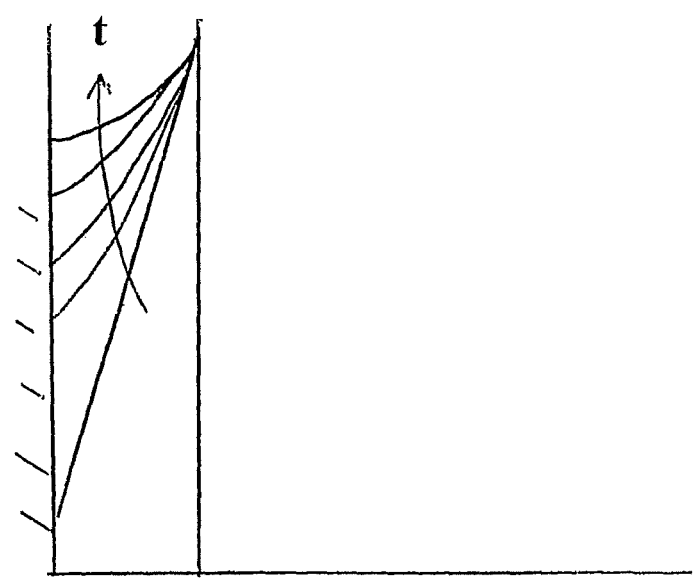

FIGS. 2A-C illustrate the events that occur at the surface of the working electrode of a biosensor during the various stages of measurement in accordance with the invention. FIG. 2A shows an instantaneous view just as the working electrode come in contact with the bodily fluid 22. The biosensor has a conductive electrode surface 20, coated with a polymer layer 21 in which enzyme E is distributed. The bodily fluid 22 contains analyte such as glucose G.

As time passes, G diffuses into the polymer layer 21, and interacts with enzyme E ultimately producing peroxide within the polymer layer. If no potential is applied at the electrode, the concentration of peroxide would be essentially uniform throughout the layer. When potential is applied, however, the concentration of peroxide changes as it is consumed at the working electrode, progressing from a curved concentration profile to a straight line over time as depicted in FIG. 2B. This corresponds to an observable Cottrell current profile, with the straight line gradient corresponding to the plateau current. Thicker polymer layers require more time to achieve the plateau current.

When the potential is turned off, the number of concentration distribution starts in the straight line distribution and decays back towards an equilibrated distribution as reflected in FIG. 2C. This change in the distribution of molecules in the polymer layer manifests itself as a decay in the potential observed at the working electrode.

Using this model for what is occurring in the polymer layer, a correction can be determined for the thickness of the polymer layer. First, the model assumes that the distribution of redox molecules (for example peroxide) under applied potential follows Cottrell-type behavior, in which case the change in concentration is related to the time as:

$$\frac{d[\text{molecules}]}{dt} \propto \frac{1}{\sqrt{t}},$$

and the current I follows the Cottrell equation, $$I = nFAC\sqrt{\frac{D}{\pi t}},$$

where n is the number of electrons, F is the Faraday constant, A is the area of the electrode and C is the concentration of the molecule. Grouping the terms n, F, A, C, D and pi into one term k, this equation can be simplified to $$I = \frac{k}{\sqrt{t}}.$$

In each of these equations, t is the time after the potential is turned off.

Assuming that I is some function of potential V, i.e., that $$f(V) \propto \frac{k}{\sqrt{t}},$$

then

-continued $$V \propto \frac{k}{\sqrt{t}},$$

and plotting the relationship of V and 1/(square root–t) should give us a slope k as a correction factor. The use of the slope k varies depending on whether the redox active molecule is part of a reversible redox couple (like ferro) or is irreversible (like $H_2O_2$). In the first case with a reversible redox couple, $$I_{corr} = I_{meas} \times \frac{1}{\sqrt{k}}.$$

In the second case, $$I_{corr} = I_{meas} \times \frac{1}{k}.$$

This approach to determination of a correction factor was validated in a model system in which coated platinum or gold electrodes (without enzyme in the coating) were placed in solutions of different concentrations of peroxide or ferrocyanide, respectively.

Figures 4A, 4B, 4C:
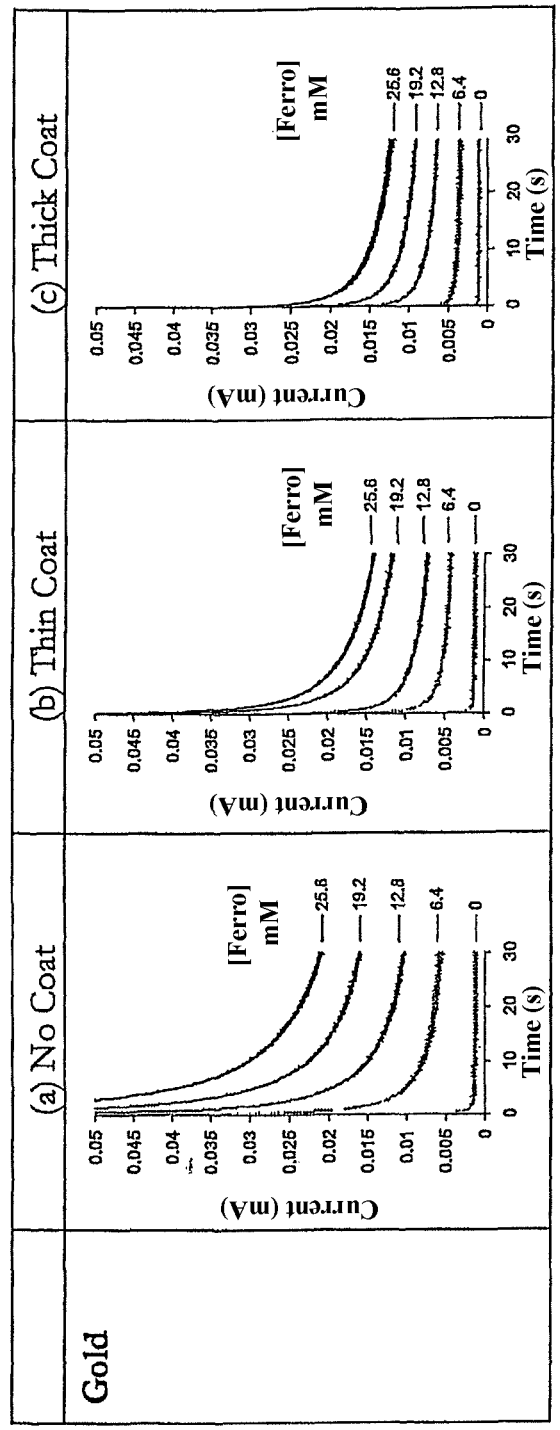
FIGS. 4A-C shows show amperometric responses of a gold electrode to different concentrations of ferrocyanide when the electrode is uncoated (FIG. 4A), thinly coated (FIG. 4B) and thickly coated (FIG. 4C).

FIGS. 3A-C shows show amperometric responses of a platinum electrode to different concentrations of $H_2O_2$ when the electrode is uncoated (FIG. 3A), thinly coated (FIG. 3B) and thickly coated (FIG. 3C) to simulate differences in the thickness of a polymer layer. As can be seen, in each case the amperometric response is dependent on the amount of $H_2O_2$ present, but the degree of dependence is different depending on the coating thickness. FIGS. 4A-C show similar results, using a gold electrode and ferro/ferricyanide electron transfer mediator. In general, a ferro/ferricyanide mediator is unlikely to be useful in an implantable electrode because of its potential toxicity unless it is restrained in the polymer layer, but its common use in in vitro glucose monitoring systems makes it a convenient model system for in vitro demonstration that the same type of results are observed in both mediated and direct reaction (like $H_2O_2$) systems.

Table 1 summarizes the results shown in FIGS. 3A-C and 4A-C.

| Electrode System | Potential Applied | Thin Coat Current Reduction (vs. no coat) | Thick Coat Current Reduction (vs. no coat) |
|---|---|---|---|
| Gold-Ferro | 450 mV | 30% | 50% |
| Platinum-$H_2O_2$ | 600 mV | 25% | 70% |

The difference in the observed current as a function of polymer layer thickness demonstrates the importance of making a correction for the thickness of the polymer layer in order to achieve an acceptable result from the measurement.

Figures 5A, 5B, 5C:
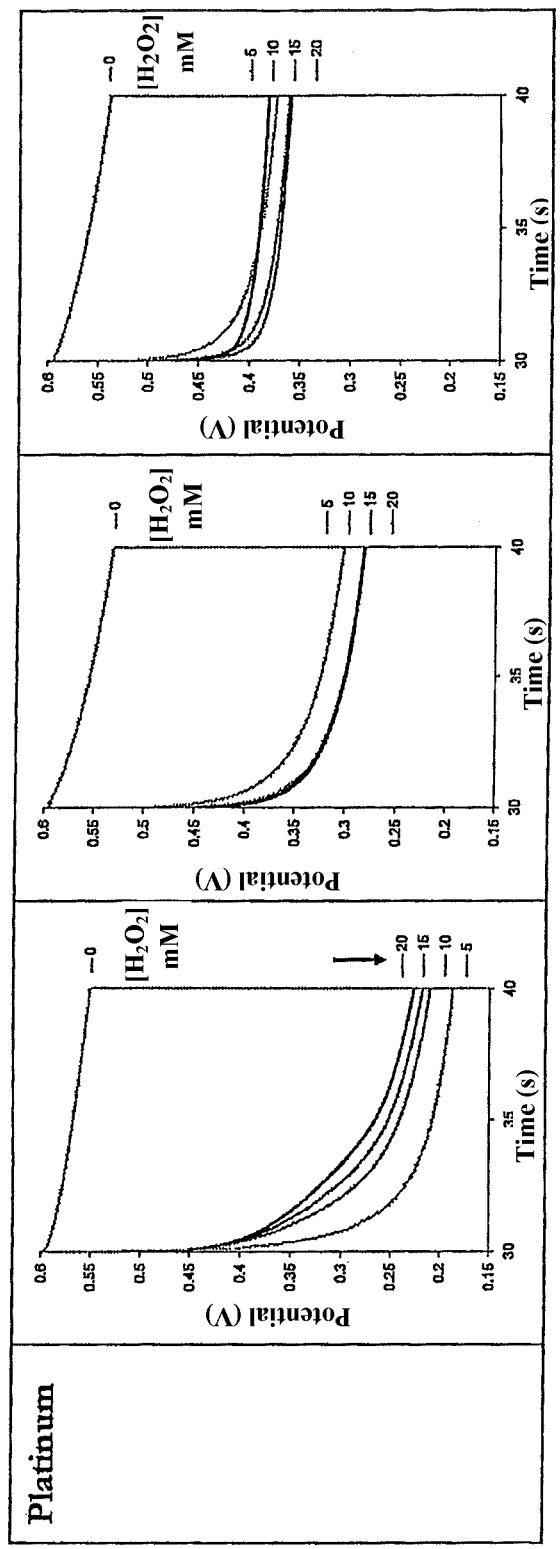
FIGS. 5A-C shows potential decay over a period of 10 seconds after potential is turned off for the platinum/$H_2O_2$ system, with uncoated, thin coated and thick coated electrodes.

In the method of the invention, after a period of applied potential (30 seconds in the case of FIGS. 3A-C and 4A-C) and observation of the current, the applied potential is turned off, and the decay of the potential is observed. FIGS. 5A-C shows this decay over a period of 10 seconds for the platinum/$H_2O_2$ system, with uncoated, thin coated and thick coated electrodes. FIGS. 6A-C shows this decay over a period of 10 seconds for the gold/ferro system, with uncoated, thin coated and thick coated electrodes. The observed variation in the potential decay as a function of the thickness of the membrane/polymer layer is consistent with the physical phenomena that occur at the electrode when the applied potential is turned off.

Figure 9B:
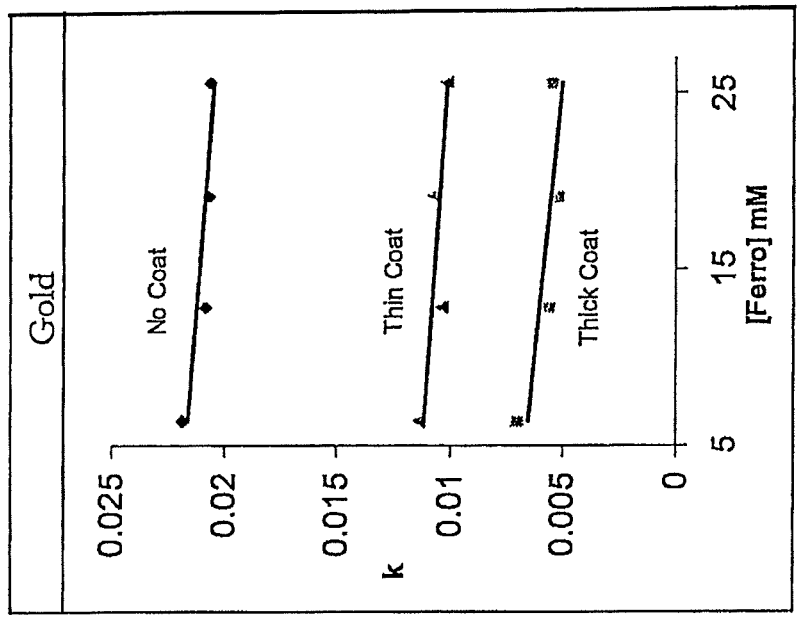
FIGS. 9A and B show determined correction factors k as a function of $H_2O_2$ and ferrocyanide concentration, respectively.
Figure 9A:
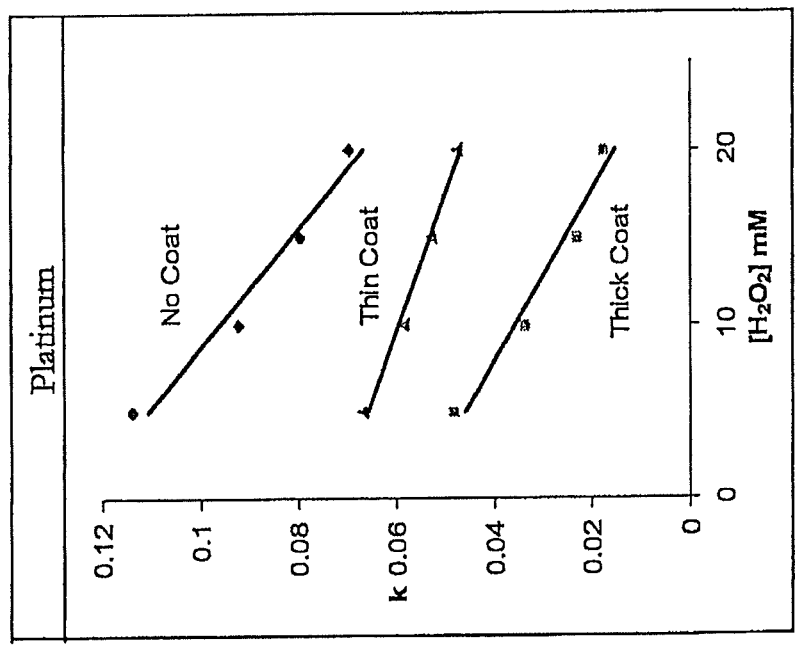

The results obtained in these tests were used to generate the graphs of V vs 1/sqrt-t in FIGS. 7A-C and 8A-C to determine the slope k. FIGS. 9A and 9B show the determined slopes, k, as a function of $H_2O_2$ and ferro concentration, respectively.

Figures 10A, 10B:
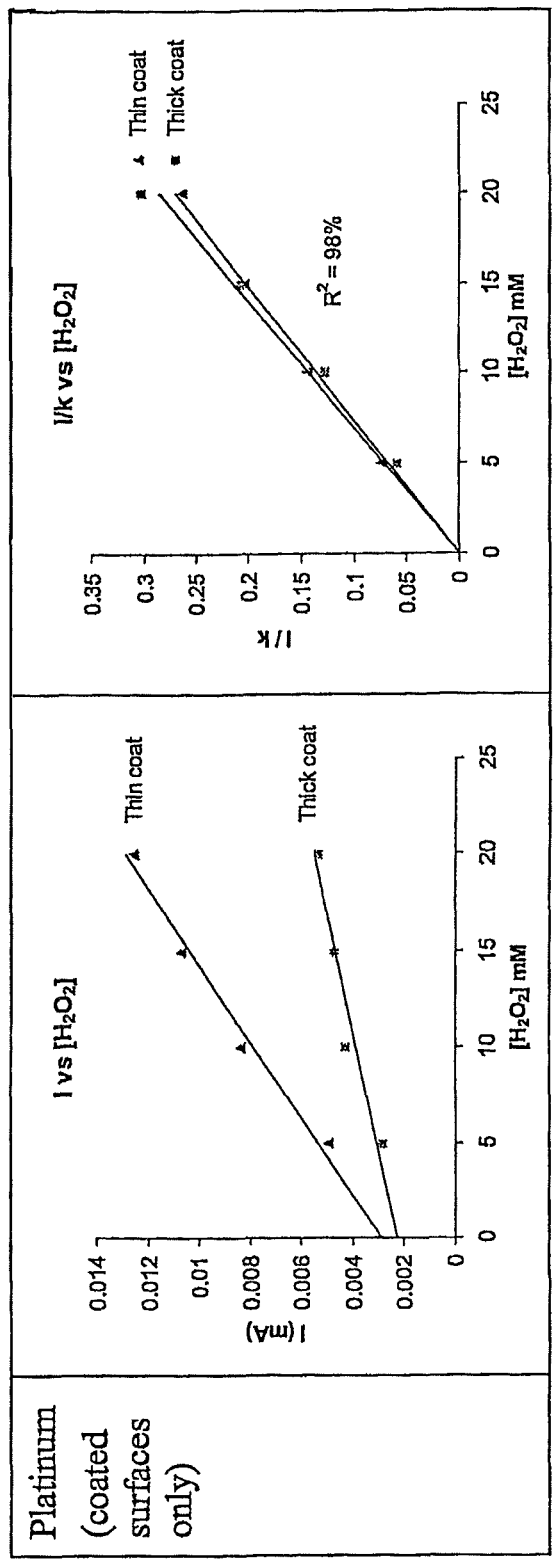
FIG. 10A shows a graph of $I_{meas}$ versus concentration of $H_2O_2$ for thin and thick coated platinum electrodes.
FIG. 10B shows a graph of $I_{corr}$ i.e., ($I_{meas}$/k) versus concentration.

FIG. 10A shows a graph of $I_{meas}$ versus concentration of $H_2O_2$ for thin and thick coated platinum electrodes. As can be seen, there is a substantial different in the observed current at any given concentration, depending on the thickness of the electrode coating. FIG. 10B shows a graph of $I_{core}$ ($I_{meas}$/k) versus concentration. The two lines in this case are essentially the same, thus showing the effectiveness of the correction factor for adjusting for the effect of membrane/polymer layer thickness.

Figures 11A, 11B:
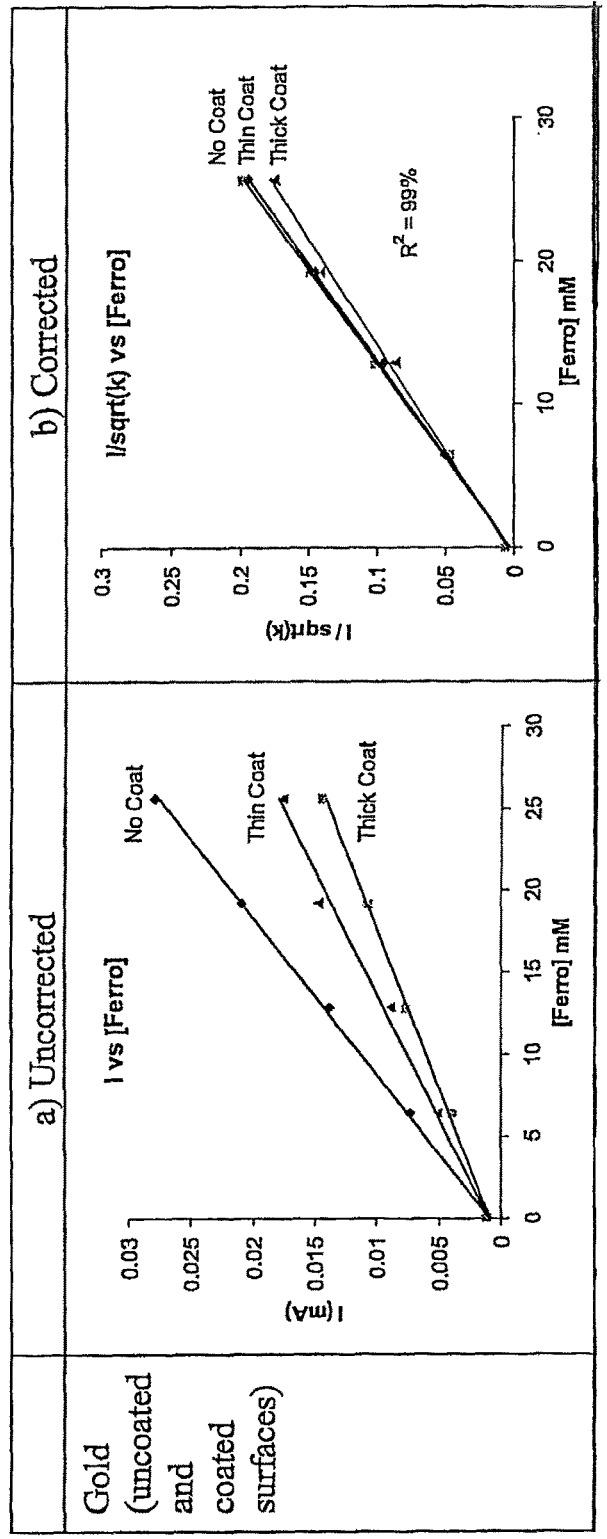
FIG. 11A shows a graph of $I_{meas}$ versus concentration of ferrocyanide for uncoated, thin coated and thick coated platinum electrodes.
FIG. 11B shows a graph of $I_{corr}$ i.e., ($I_{meas}$/sqrt-k), versus concentration.

FIG. 11A is a graph of $I_{meas}$ versus concentration of ferrocyanide for uncoated, thin coated and thick coated gold electrodes. As can be seen, there is a substantial different in the observed current at any given concentration, depending on the thickness of the electrode coating. FIG. 11B shows a graph of $I_{core}$ ($I_{meas}$/sqrt-k) versus concentration. The three lines in this case are essentially the same, thus showing the effectiveness of the correction factor for adjusting for the effect of membrane/polymer layer thickness.

From this, it can be seen that the present invention provides a method for correcting the signal obtained form a biosensor in which the working electrode comprises a polymer layer containing an enzyme that reacts with the analyte to produce a redox active species that takes into account variations in the thickness of the polymer layer. In accordance with this method, the presence or concentration of an analyte is determined by:

(a) placing a solution to be tested for analyte in contact with a biosensor comprising an electrode and a polymer layer containing an enzyme, (b) applying a potential to the biosensor sufficient to oxidize or reduce a redox active species and generate a current, (c) observing the current to arrive at a measured current value, $I_{meas}$, (d) switching off the applied potential and observing subsequent decay of potential to obtain a plurality of V versus t data points, (e) determining the slope k of a plot of V versus 1/sqrt-t, and (f) applying a correction factor to the measured current $I_{meas}$ to arrive at a corrected current, $I_{corr}$, wherein the correction factor is 1/k if the redox active species is part of a reversible redox couple, and 1/sqrt-k if the redox active species is part of an irreversible redox couple, and (g) determining the presence or concentration of the analyte from the corrected current, $I_{corr}$.

Figure 12A:
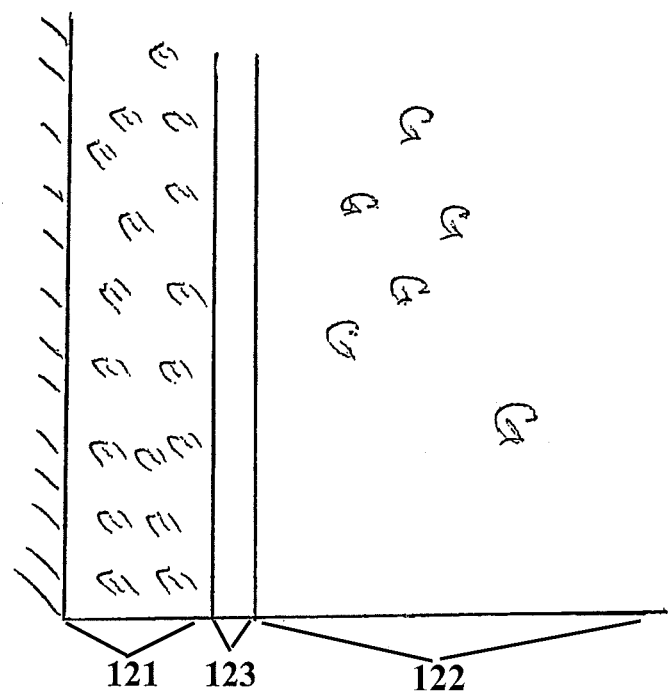
FIGS. 12A and B shows a schematic representation of an electrode with a polymer layer and an additional coating layer.

This same type of correction factor can also be applied to correct for increases in thickness that arise from additional coating layers or electrode fouling. FIG. 12A shows a schematic representation of a working enzyme electrode in which the enzyme-containing polymer layer 121 has an additional coating layer 123 disposed on it. This might be an additional coating such as a biocompatability layer as disclosed in U.S. Pat. No. 6,514,718 or it might be a layer of fouling due to time spent implanted. For measurement to occur, the analyte such as glucose G must diffuse through layer 123 to reach the enzyme-containing polymer layer 121. Similarly, the redox active species such as peroxide must diffuse out through the layer 123 before it can escape from the vicinity of the electrode and into the bodily fluid 122. The polymer layer and the additional layer are both regions of limited mobility that can be considered to be contiguous when compared with the bodily fluid 122 where a chemical component can readily diffuse away from the surface of the electrode and cease to be part of the measurement.

Figure 12B:
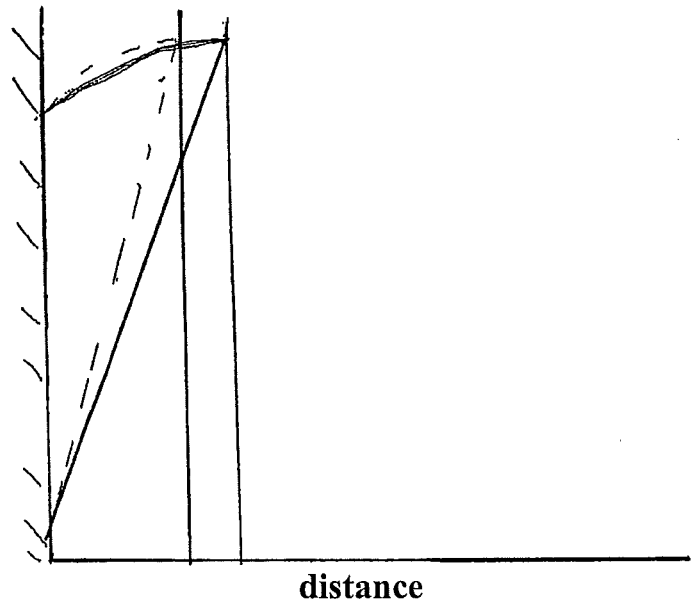

FIG. 12B shows a modification of FIG. 2B to take into account the additional thickness of the layer. When potential is applied, the concentration of peroxide changes as it is consumed at the working electrode, progressing from a curved concentration profile to a straight line over time. However, because of the increased thickness of the layer, the time required to reach this straight line is greater as reflected in the solid line 125 as compared to the dashed line 126. This, same thing manifests itself in the time course of the observed potential decay so that there are observable differences in the plot of V versus 1/sqrt-t whether the thickness variation is in the polymer layer itself or an additional coating layer.

Figures 13A, 13B:
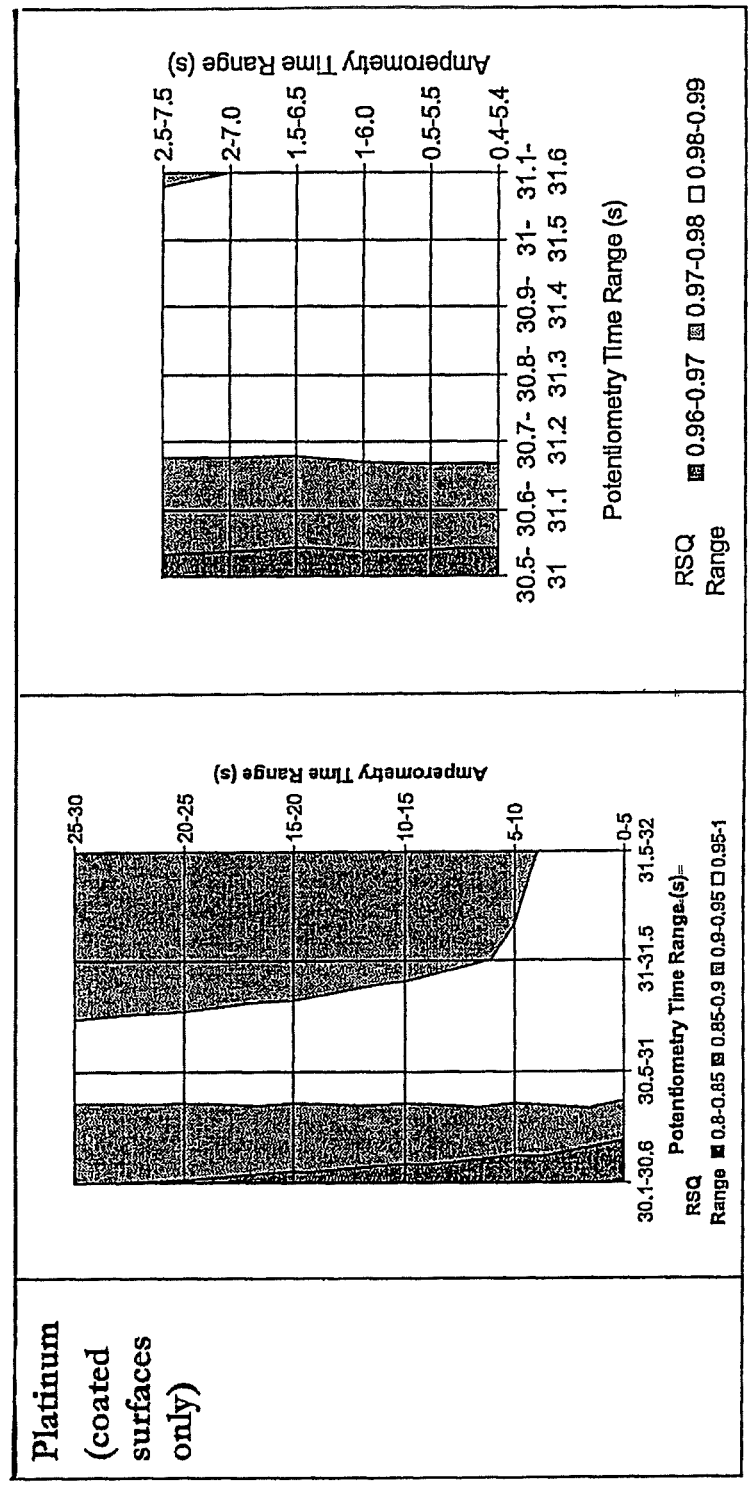
FIGS. 13A and B show the R-squared value at different combinations of potentiometry and amperometry times for platinum electrodes and $H_2O_2$.
Figures 14A, 14B:
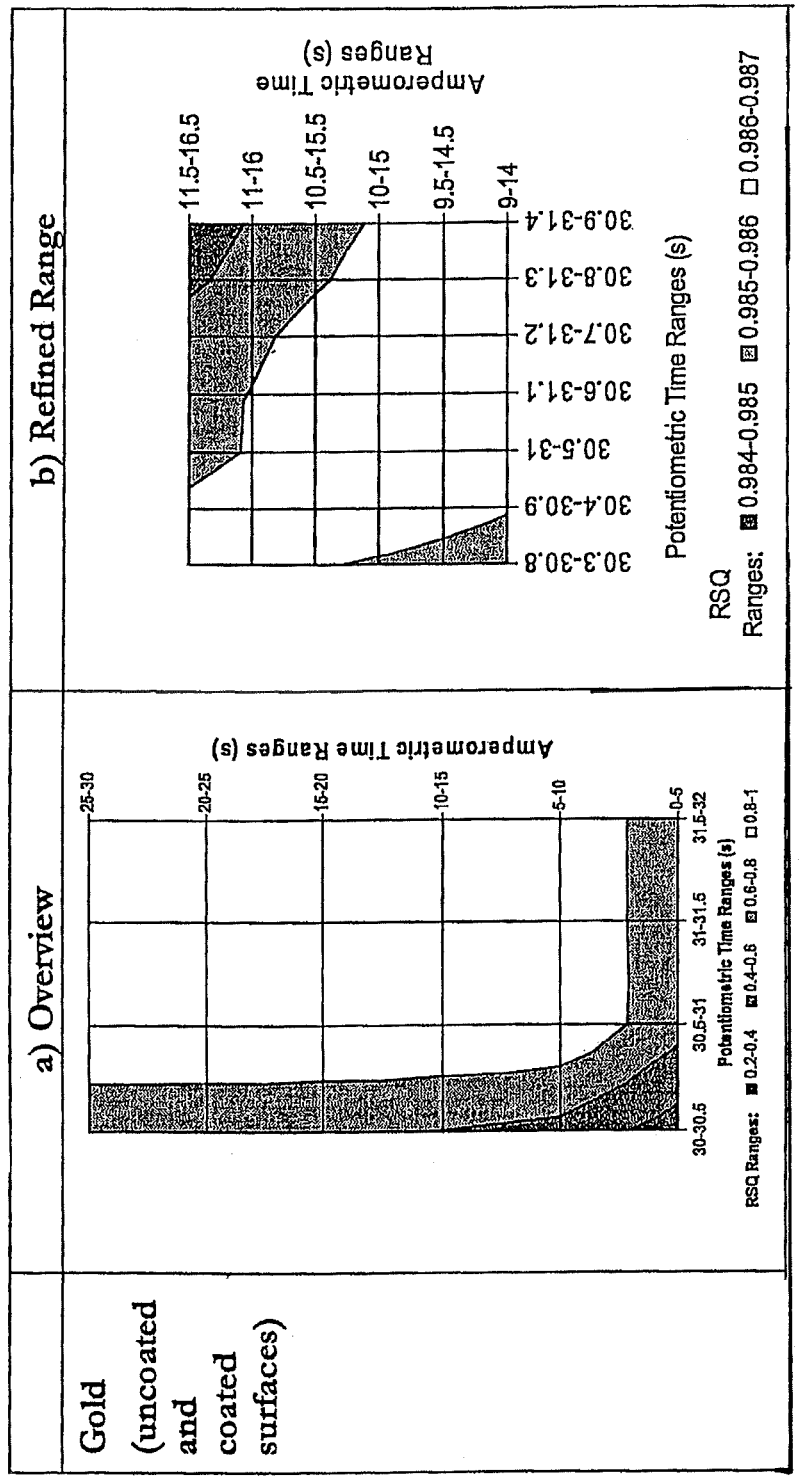
FIGS. 14A and B show the R-squared value at different combinations of potentiometry and amperometry times for gold electrodes and ferrocyanide.

The data discussed above used a consistent amperometry time of 30 seconds and a potentiometry time of 10 seconds for both types of electrodes (gold and platinum), and for both reversible and irreversible systems The specific times that are optimum in terms of providing the best correction need not in fact be the same. Using the same data, regression analysis between the current (I), the correction factor k and different amperometry and potentiometry times to determine the best fit of the parameters based on the correction function used. FIGS. 13A and B show the R-squared value at different combinations of potentiometry and amperometry times for platinum electrodes and $H_2O_2$. FIGS. 14A and B show the R-squared value at different combinations of potentiometry and amperometry times for gold electrodes and ferrocyanide. As is apparent, the ranges that provide the greatest correlation in the corrected data (white area of plot) are somewhat different.

In particular, for the platinum/$H_2O_2$ determinations, use of current measurements from shorter amperometry time intervals (less than 10 seconds) is preferred, and intermediate potentiometry times are optimal. In contrast, the best results with the gold electrodes are obtained over a broader range of time combinations.

Figure 15A:
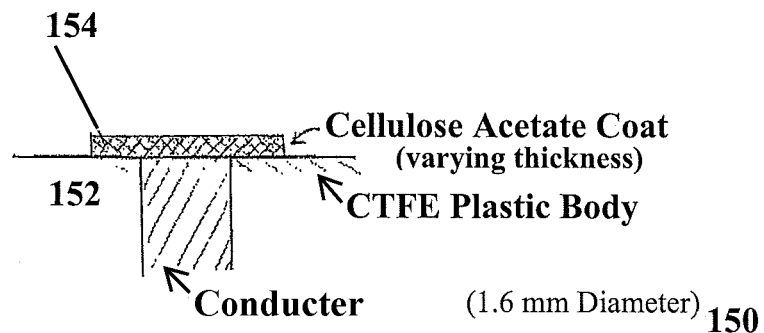
FIGS. 15A and B show views of an embodiment of an implantable electrode with which the invention can be used
Figure 15B:
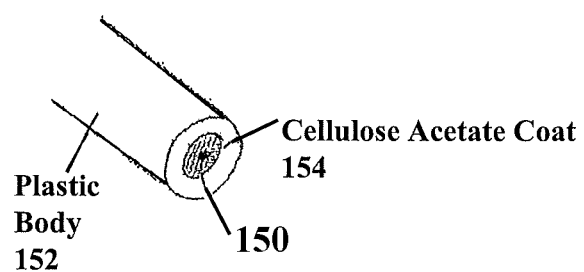

The present invention can be used to improve the accuracy of any electrochemical analysis that uses a membrane coated biosensor. However, it is particularly applicable for use with implantable electrodes. FIGS. 15A and B show views of an embodiment of an implantable electrode with which the invention can be used, although it should be understood that the invention not limited to use with any particular electrode design. As depicted, the electrode has a conductor 150 for example a platinum or gold wire with a diameter of 1.6 mm encased in a plastic body 152. The plastic body is suitably made from chlorotrifluoroethylene (CTFE) although other biocompatible thermoplastics may also be used. The end of the conductor 150 is exposed at the end of the plastic body 152, but is covered by a membrane coating 154. In some embodiments, this membrane coating is suitably cellulose acetate but other biocompatible materials may also be used. The membrane coating 154 contains the appropriate enzyme for the analyte to be measured, for example glucose oxidase or pyrroloquinoline quinone glucose dehydrogenase (PQQ) in the case of glucose measurement; lactate oxidase in the case of lactate as the analyte or cholesterol oxidase for measurement of cholesterol. In other embodiments, the sensor may include additional layers, such as a top coat layer to enhance biocompatability.

The electrode is placed in contact with the body fluid in which the analyte is to be measured, for example by subcutaneous or intravascular implantation, in combination with stents or implanted stimulation devices or exterior to the body but in contact with a body fluid (such as interstitial fluid) and used to detect the analyte and the detected signal is corrected in accordance with the present invention to account for thickness and/or fouling at the time of the measurement.

Based on the foregoing, it can be seen the present invention provides significant advances over the art, including the following:

(1) a method for correcting readings obtained from an electrochemical sensor having a coating layer to correct for the thickness of the coating layer, wherein the coating layer may be one or more layers of polymeric coating applied to an electrode within the sensor as part of its manufacture and/or fouling arising from the placement of the sensor in contact with a fluid to be analyzed.

(2) an implantable electrochemical sensor system in which the method of the invention is performed to correct the readings. The sensor may be employed solely for producing informational measurements as to the presence/concentration of a particular or it may be linked to an operational system component such as an insulin pump or a device such cardiac stimulation with the output of the device being controlled in whole or in part by parameters measured by the sensor system.

The invention provides multiple advantages because of its ability to correct for variations in the coating thickness the electrode of a sensor. It can (1) reduce the cost of the sensor because manufacturing tolerances on applied coating thicknesses do not have to be as precise; and (2) increase sensor lifetime, because correct readings can be obtained for a greater period of time, even if fouling occurs. This not only decreases the cost as a consequence of using fewer sensors, but it decreases the cost of disease management because fewer implantations are required.

The invention claimed is:

1. An implantable electrochemical sensor system comprising:
    a biosensor comprising an electrode and a polymer layer having a thickness and containing an enzyme;
    a source configured to apply a potential (V) to the biosensor, said potential being sufficient to oxidize or reduce a redox active species in the solution and generate a current;
    a controller configured to control the source;
    a potentiometer configured to collect potential measurements at a plurality of different times after application of potential ceases;
    logic configured to determine the thickness of the polymer layer; and
    an output device configured to communicate results determined by the logic.

2. The system of claim 1, wherein the redox active species is a part of a reversible redox couple and the thickness of the polymer layer is proportional to $1/k$.

3. The system of claim 2, wherein the logic is further configured to determine a correction factor for the thickness of the polymer layer based on the slope (k) of a plot of V versus $1/\sqrt{t}$.

4. The system of claim 1, wherein the redox active species is part of an irreversible redox couple and the thickness of the polymer layer is proportional to $1/\sqrt{k}$.

5. The system of claim 4, wherein the logic is further configured to provide a corrected measure of analyte in the sample.

6. The system of claim 5, wherein the system further comprises an operational system component configured to receive one or more control parameters determined by the logic.

7. The system of claim 6, wherein the operational system component is an insulin pump.

8. The system of claim 6, wherein the operational system component is a cardiac stimulator.

9. The system of claim 1, wherein the electrode is platinum.

10. The system of claim 1, wherein the electrode is gold.

11. The system of claim 1, wherein, for a particular determination of analyte, the potential is applied to the biosensor for a period of 60 seconds or less.

12. The system of claim 11, wherein the potential is applied to the biosensor for a period of 40 seconds or less.

13. The system of claim 12, wherein the potential is applied to the biosensor for a period of 10 to 30 seconds.

14. The system of claim 11, wherein the potential measurements are collected during a period that is 5 seconds or less after switching off the applied potential.

15. The system of claim 14, wherein the potential measurements are collected during a period of time that is 2 seconds or less after switching off the applied potential.

16. The system of claim 1, wherein the system further comprises an operational system component configured to receive one or more control parameters determined by the logic.

17. The system of claim 16, where the operational system component is an insulin pump.

18. The system of claim 16, wherein the operational system component is a cardiac stimulator.

19. An implantable electrochemical sensor system comprising:
- a biosensor comprising an electrode and a polymer layer having a thickness and containing an enzyme;
- a source configured to apply a potential (V) to the biosensor, said potential being sufficient to oxidize or reduce a redox active species in the solution and generate a current;
- a controller configured to control the source;
- a potentiometer configured to collect potential measurements at a plurality of different times after application of potential ceases;
- logic configured to determine the thickness of the polymer layer;
- an output device configured to communicate results determined by the logic; and
- an operational system component configured to receive one or more control parameters configured by the logic.

20. The system according to claim 19, wherein the logic is further configured to determine a measure of analyte that is corrected based on the determination of the thickness of the polymer layer.

* * * * *